US012564401B1

(12) United States Patent
Nosrati et al.

(10) Patent No.: US 12,564,401 B1
(45) Date of Patent: Mar. 3, 2026

(54) AUTOMATED SURGICAL STAPLE INSPECTION SYSTEM

(71) Applicant: Cilag GmbH International, Zug (CH)

(72) Inventors: Reyhaneh Nosrati, Boston, MA (US); Chad Steven Lape, Sr., Mason, OH (US); Scott A. Jenkins, Mason, OH (US); Francesca Mayhaus, Independence, KY (US); Jorge Adrian Dayer Carrillo, Cincinnati, OH (US); Carlos Ivan Ramirez Martinez, Juarez (MX); Anu Ahuja, Raritan, NJ (US); Saman Sarraf, San Jose, CA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/007,353

(22) Filed: Dec. 31, 2024

(51) Int. Cl.
A61B 17/00 (2006.01)
A61B 17/064 (2006.01)
(Continued)

(52) U.S. Cl.
CPC .... A61B 17/07207 (2013.01); A61B 17/0644 (2013.01); G06T 7/0012 (2013.01); G06T 7/73 (2017.01); G06V 10/764 (2022.01); G06V 10/774 (2022.01); G06V 20/698 (2022.01); A61B 2017/00725 (2013.01); A61B 2017/07271 (2013.01); G06T 2207/10056 (2013.01); G06T 2207/20081 (2013.01); G06T 2207/30088 (2013.01); G06V 2201/034 (2022.01)

(58) Field of Classification Search
CPC .......... B25D 16/006; B25D 2216/0023; F04D 25/06; H02K 7/14; H05K 1/0204; H05K 3/284; H05K 7/20154; H05K 2201/066; H05K 7/20436; H05K 7/20463; H05K 7/20409
USPC ......... 227/175.1–182.1, 8, 19; 606/139, 142, 606/143, 205–208
See application file for complete search history.

(56) References Cited

U.S. PATENT DOCUMENTS 5,441,191 A * 8/1995 Linden .................. B25C 5/1689
227/120
5,507,425 A * 4/1996 Ziglioli ................. B25C 5/1689
227/127

(Continued)

FOREIGN PATENT DOCUMENTS

WO WO-2019190405 A1 * 10/2013 ........... F16B 1/0071

*Primary Examiner* — Robert F Long
(74) *Attorney, Agent, or Firm* — Amsel IP Law PLLC; Jason Amsel

(57) ABSTRACT

An automated surgical staple inspection system automatically generates surgical staple inspection data characterizing a set of staples fired into a test skin by stapling device in a staple test. An inspection processing device obtains one or more images of the set of staples and applies an object detection model to infer locations of the staples and respective classes of the staples indicating whether the staples are properly formed or have one or more identified defects. Based on the inferred locations, staples may be mapped to respective positions in an expected staple pattern to generate a staple map. A keypoint detection model furthermore operates to automatically identify a set of keypoints in each staple from which staple height may be determined. The inspection processing device may generate one or more digital reports based on the inspection data, which may be outputted to a user interface of a user device.

20 Claims, 14 Drawing Sheets

(51) Int. Cl.

| | |
|---|---|
| *A61B 17/072* | (2006.01) |
| *G06T 7/00* | (2017.01) |
| *G06T 7/73* | (2017.01) |
| *G06V 10/764* | (2022.01) |
| *G06V 10/774* | (2022.01) |
| *G06V 20/69* | (2022.01) |

(56) References Cited

U.S. PATENT DOCUMENTS

| | | | | |
|---|---|---|---|---|
| 7,747,311 | B2 * | 6/2010 | Quaid, III | A61B 34/74 |
| | | | | 345/157 |
| 8,770,312 | B2 * | 7/2014 | Kume | B23Q 17/20 |
| | | | | 173/4 |
| 10,513,015 | B2 * | 12/2019 | Lefavour | B25B 17/00 |
| 11,611,186 | B2 * | 3/2023 | Ruch | B25B 27/146 |
| 11,986,183 | B2 * | 5/2024 | Yates | A61B 34/37 |
| 2006/0219752 | A1 * | 10/2006 | Arad | A61B 17/07207 |
| | | | | 227/176.1 |
| 2009/0114701 | A1 * | 5/2009 | Zemlok | A01H 6/749 |
| | | | | 227/176.1 |
| 2009/0206135 | A1 * | 8/2009 | Hall | A61B 17/07207 |
| | | | | 227/176.1 |
| 2010/0096431 | A1 * | 4/2010 | Smith | A61B 17/115 |
| | | | | 227/175.2 |
| 2011/0036891 | A1 * | 2/2011 | Zemlok | A61B 17/07207 |
| | | | | 227/176.1 |
| 2013/0175318 | A1 * | 7/2013 | Felder | A61B 17/115 |
| | | | | 227/175.1 |
| 2014/0166718 | A1 * | 6/2014 | Swayze | A61B 17/1155 |
| | | | | 227/175.1 |
| 2015/0265358 | A1 * | 9/2015 | Bowling | A61B 34/30 |
| | | | | 700/261 |
| 2016/0256186 | A1 * | 9/2016 | Shelton, IV | A61B 17/295 |
| 2016/0363510 | A1 * | 12/2016 | Kanack | B25B 27/10 |
| 2016/0374672 | A1 * | 12/2016 | Bear | H02J 7/00 |
| | | | | 606/219 |
| 2018/0168602 | A1 * | 6/2018 | Bakos | A61B 17/2816 |
| 2018/0250002 | A1 * | 9/2018 | Eschbach | A61B 17/0682 |
| 2019/0160643 | A1 * | 5/2019 | Lefavour | B25F 5/005 |
| 2021/0328399 | A1 * | 10/2021 | Radtke | B25F 5/02 |
| 2022/0233251 | A1 * | 7/2022 | Bowling | A61B 34/20 |
| 2022/0288754 | A1 * | 9/2022 | Zhou | B25B 27/10 |
| 2022/0407274 | A1 * | 12/2022 | Radtke | H01R 43/0486 |
| 2024/0023967 | A1 * | 1/2024 | Valentine, Jr. | A61B 17/1155 |
| 2024/0246215 | A1 * | 7/2024 | Burnett | B25F 3/00 |
| 2024/0246219 | A1 * | 7/2024 | Skinner | B25H 3/003 |
| 2024/0273985 | A1 * | 8/2024 | Turner | G08B 13/2405 |
| 2024/0349232 | A1 * | 10/2024 | White, Jr. | B25F 5/00 |
| 2024/0422220 | A1 * | 12/2024 | Davis | H04L 67/12 |

* cited by examiner

Annotated
Training
Image
400

Staple
408

Keypoints
406

402
Fail

404
Pass

802
Detected
Fail

804
Detected
Pass

Cutline Distance
1006

Cutline Start
1004

Cutline
1002

Staple Height Report

1202 Staple ID  
1204 Leg ID  
1206 Height Estimate

| Staple ID | Leg ID | Height Estimate |
|---|---|---|
| 1 | 1 | 1.58 |
| | 2 | 1.30 |
| | 3 | 1.40 |
| | 4 | 1.49 |
| | 5 | 1.43 |
| | 6 | 1.53 |
| | 7 | 1.41 |
| | 8 | 1.49 |
| | 9 | 1.32 |
| | 10 | 1.38 |
| | 11 | 1.38 |
| | 12 | 1.47 |
| | 13 | 1.39 |
| | 14 | 1.44 |
| 15 | 15 | 1.18 |
| | 16 | 1.37 |
| | 17 | 1.20 |
| | 18 | 1.38 |
| | 19 | 1.21 |
| | 20 | 1.41 |
| | 21 | 1.18 |
| | 22 | 1.49 |
| | 23 | 1.92 |
| | 24 | 1.53 |
| | 25 | 1.33 |
| | 26 | 1.41 |
| | 27 | 1.54 |
| | 28 | 1.39 |
| 29 | 43 | 1.23 |
| | 44 | 1.44 |
| | 45 | 1.32 |
| | 46 | 1.40 |
| | 47 | 1.36 |
| | 48 | 1.37 |
| | 49 | 1.16 |
| | 50 | 1.42 |
| | 51 | 1.35 |
| | 52 | 1.17 |
| | 53 | 1.18 |
| | 54 | 1.32 |
| | 55 | 1.30 |
| | 56 | 1.20 |
| | 57 | 1.20 |
| | 58 | 1.34 |
| 30 | 31 | 1.37 |
| | 32 | 1.38 |
| | 33 | 1.35 |
| | 34 | 1.34 |
| | 35 | 1.30 |
| | 36 | 1.30 |
| | 37 | 1.92 |
| | 38 | 1.18 |
| | 39 | (shaded) |
| | 40 | (shaded) |
| | 41 | 1.32 |
| | 42 | 1.44 |
| 44 | 85 | 1.33 |
| | 86 | 1.90 |
| | 87 | 1.34 |
| | 88 | 1.19 |
| 45 | 90 | (shaded) |
| | 91 | 1.24 |
| | 92 | 1.21 |
| | 93 | 1.23 |
| | 94 | 1.22 |
| | 95 | 1.30 |
| | 96 | 1.21 |
| | 97 | 1.26 |
| | 98 | 1.21 |
| | 99 | 1.23 |
| | 100 | 1.22 |
| | 101 | 1.27 |
| | 102 | 1.24 |
| | 103 | 1.24 |
| | 104 | 1.21 |
| | 105 | 1.24 |
| | 106 | 1.24 |
| | 107 | 1.20 |
| | 108 | 1.23 |
| | 109 | 1.23 |
| | 110 | 1.20 |
| | 111 | 1.23 |
| | 112 | 1.24 |
| | 113 | 1.22 |
| | 114 | 1.22 |
| | 115 | 1.23 |
| | 116 | 1.32 |
| | 117 | 1.35 |
| | 118 | 1.18 |
| 46 | 61 | 1.21 |
| | 62 | 1.23 |
| | 63 | 1.26 |
| | 64 | 1.29 |
| | 65 | 1.32 |
| | 66 | 1.27 |
| | 67 | 1.28 |
| | 68 | 1.28 |
| | 69 | 1.28 |
| | 70 | 1.29 |
| | 71 | 1.28 |
| | 72 | 1.28 |
| | 73 | 1.29 |
| | 74 | 1.28 |
| | 75 | 1.29 |
| | 76 | 1.28 |
| | 77 | 1.28 |
| | 78 | 1.28 |
| | 79 | 1.25 |
| | 80 | 1.26 |
| | 81 | 1.22 |
| | 82 | 1.24 |
| | 83 | 1.29 |
| | 84 | 1.26 |
| 119 | 120 | 1.29 |
| | 121 | 1.26 |
| | 122 | 1.23 |
| | 123 | 1.24 |
| | 124 | 1.25 |
| | 125 | 1.26 |
| | 126 | 1.27 |
| | 127 | 1.28 |
| | 128 | 1.29 |
| | 129 | 1.30 |
| | 130 | 1.31 |
| | 131 | 1.32 |
| | 132 | 1.30 |
| | 133 | (shaded) |
| | 134 | (shaded) |
| | 135 | 1.28 |
| | 136 | 1.31 |
| | 137 | 1.32 |
| | 138 | 1.31 |
| | 139 | 1.21 |
| | 140 | 1.32 |
| | 141 | 1.31 |
| | 142 | 1.28 |
| | 143 | 1.31 |
| | 144 | 1.20 |
| | 145 | 1.19 |
| | 146 | 1.30 |
| | 147 | 1.38 |
| | 148 | 1.21 |
| 149 | 150 | 1.51 |
| | 151 | 1.43 |
| | 152 | 1.43 |
| | 153 | 1.49 |
| | 154 | 1.43 |
| | 155 | 1.46 |
| | 156 | 1.42 |
| | 157 | 1.44 |
| | 158 | 1.43 |
| | 159 | 1.43 |
| | 160 | 1.43 |
| | 161 | 1.40 |
| | 162 | 1.44 |
| | 163 | 1.44 |
| | 164 | 1.42 |
| | 165 | 1.43 |
| | 166 | 1.46 |
| | 167 | 1.42 |
| | 168 | 1.42 |
| | 169 | 1.43 |
| | 170 | 1.44 |
| | 171 | 1.43 |
| | 172 | 1.43 |
| | 173 | 1.44 |
| | 174 | 1.53 |
| | 175 | 1.43 |
| | 176 | 1.43 |

FIG. 12

AUTOMATED SURGICAL STAPLE INSPECTION SYSTEM

BACKGROUND

Surgical stapling devices are commonly used in various types of medical procedures to seal tissue and control loss of blood or other fluids. Failures in stapling devices such as misfired staples, malformed staples, and/or staples formed to improper staple heights can have significant impact on the success of a medical procedure and the patient's health outcome. In order to mitigate risks of improper operation, stapling devices may be regularly tested at a manufacturing facility or other testing site. These tests may conventionally involve firing staples into a test skin (e.g., a plastic material simulating human tissue) and manually inspecting the resulting staple patterns to determine a pass/fail for the test. However, conventional inspection processes are slow, are subject to human interpretation, and do not provide fine-grained granularity relating to specific failures.

BRIEF DESCRIPTION OF THE DRAWINGS

FIG. 12 is a second example of inspection data that may be included in a digital report generated by an automated stapler inspection system.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made to several embodiments, examples of which are illustrated in the accompanying figures. Wherever practicable, similar or like reference numbers may be used in the figures and may indicate similar or like functionality.

An automated surgical staple inspection system automatically generates surgical staple inspection data characterizing a set of staples fired into a test skin by stapler device during a staple test. An inspection processing device obtains one or more images of the set of staples and applies an object detection and classification model (trained according to a machine learning process) to infer locations of the staples and respective classes of the staples indicating whether the staples are properly formed or have one or more classes of defects. Based on the inferred locations, a staple map may be generated by mapping the respective locations to respective positions in an expected staple pattern. A keypoint detection model (trained according to another machine learning process) furthermore operates to automatically identify a set of keypoints in each staple from which staple height may be determined. The inspection processing device may generate one or more digital reports based on the inspection data, which may be outputted to a user interface of a user device.

The inspection data may furthermore be used in conjunction with identified defects in the stapler device and/or cartridges to train a defect classification model that enables specific classes of defects to be automatically identified from the inspection data. Furthermore, the inspection data may be used in conjunction with design characteristics associated with the stapler device and/or cartridges to train a device characterization model that enables inspection data to be predicted from device design characteristics, thereby enabling tests to be simulated.

Figure 1:
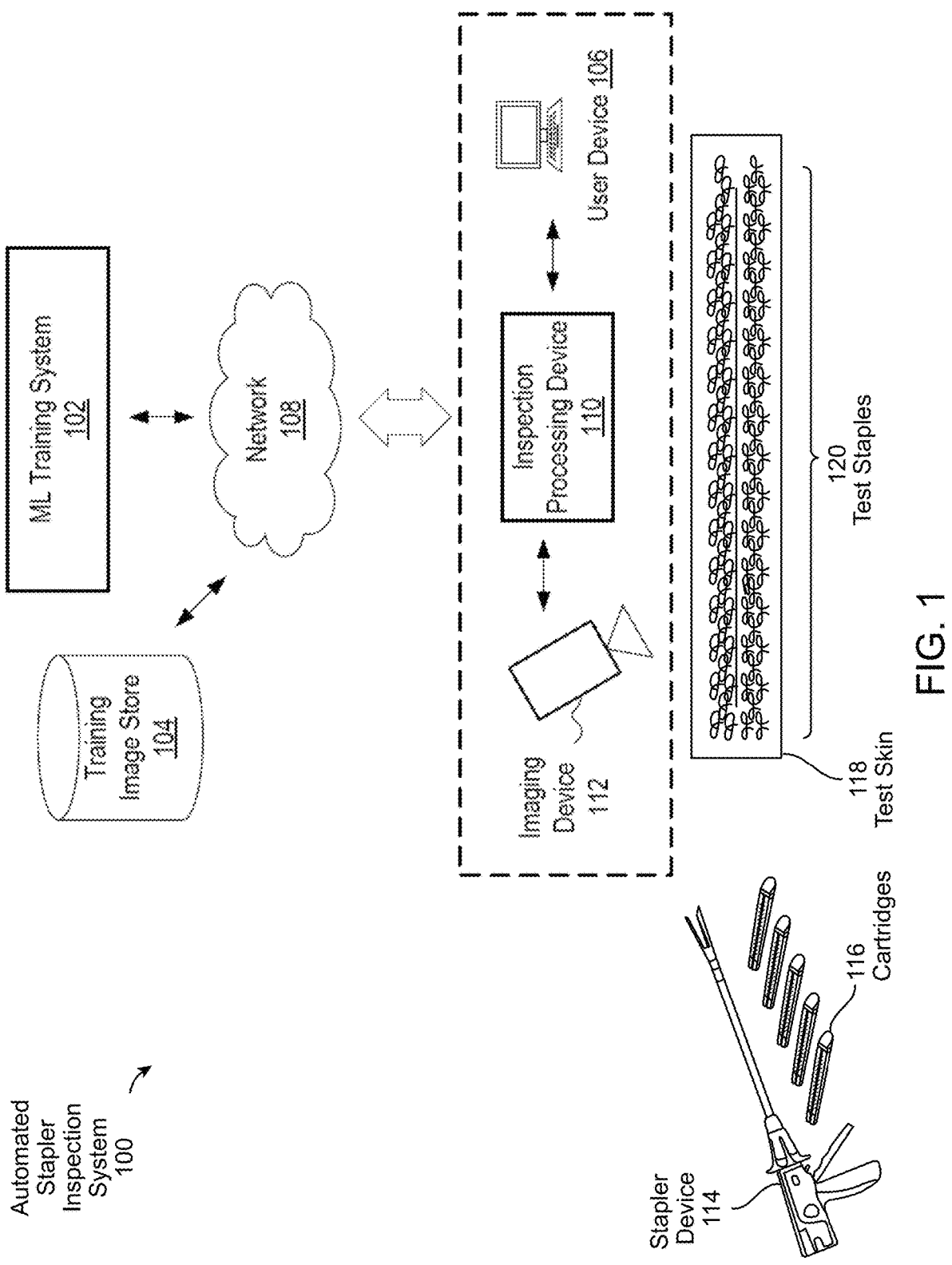
FIG. 1 is an example of a computing environment for automatically generating staple inspection data from images of a set of test staples fired into a test skin.

FIG. 1 illustrates an example implementation of a computing environment for an automated stapler inspection system 100 that performs automatic inspection of a set of test staples 120. The test staples 120 may be fired into a test skin 118 from a staple cartridge 116 by a stapler device 114. Digital images of the test staples 120 may be captured and automatically inspected to characterize the test staples 120 and evaluate performance of the stapler device 114 and/or cartridge 116.

The stapler device 114 may comprise any device for firing surgical staples. One such type of stapler device 114 is an endocutter device that simultaneously cuts and staples tissue in multiple rows on either side of the cutline. In other cases, the stapler device 114 may be a standalone surgical stapler that does not necessarily perform concurrent cutting.

The stapler device 114 fires staples from reloadable cartridges 116. In operation, a cartridge is loaded in the stapler device 114 and the stapler device 114 is activated (e.g., by squeezing a handle or pulling a trigger) to fire the staples. The firing mechanism is designed to push the staples out from the cartridge 116 through the tissue and into pre-formed grooves in the stapler device 114 that bend the staples in a manner intended to seal the tissue. For example, under proper operation, the stapler device 114 bends both ends of the staplers into loops forming a "B" shape. Different surgical applications may utilize staples of different lengths, thicknesses, or other characteristics, which may come preloaded in different stapler cartridges 116. The stapler device 114 may therefore interoperate with different types of cartridges 116 that house staplers of different sizes or other different characteristics.

The expected staple pattern from a properly operating stapler device 114 may be specific to the type of stapler device 114 and/or the cartridge 116. For example, an expected stapler pattern for an endocutter device may include three rows of staples on each side of a cutline where the rows are arranged symmetrically about the cutline. In each set of three rows, the first and last row may have staples substantially aligned and the middle row may be offset (e.g., the center of each middle row staple may be approximately halfway between the centers of adjacent staples in the first and last rows). The rows may have different numbers of staples. In one such example, the furthest rows on either side of the cutline may include 14 staples each, while the middle row and closest row on each side of the cutline may include 15 staples each. The expected staple pattern may furthermore include a range of expected staple heights measured from the crown (straight part of the "B" shape) to the peaks (highest point of the looped legs). For endocutter devices, the expected staple pattern may also include an expected cutline length representing a distance from the edge of the staple rows to the start of the cutline.

While FIG. 1 illustrates one possible staple pattern as described above, the expected pattern may vary for different types of stapler devices 114 and/or different stapler cartridges 116. For example, different stapler devices 114 and/or cartridges 116 may produce staple patterns with different numbers of rows, different numbers of staples per row, different offsets and/or expected positions of staples in each row, different staple heights, and different cutline lengths and/or positions.

The stapler device 114 and staple cartridges 116 may often be sensitive to certain manufacturing parameters associated with components of the stapler device 114 and/or the stapler cartridges 116. For example, if elements of the stapler device 114 and/or associated cartridges 116 are manufactured outside of certain specifications (e.g., too large or too small, wrong shape, too rigid or too flexible, etc.), the stapler device 114 may malfunction, causing staples to be misfired (i.e., missing from the staple pattern), malformed, or fired to a height outside of a specified height range. For endocutter devices, defects may also cause the cutline to be mispositioned relative to the staple pattern. The stapler device 114 and staple cartridges 116 may be tested for these types of defects during an inspection process in which a stapler device 114 fires a set of test staples 120 into a test skin 118 (e.g., a synthetic material that simulates human tissue). The set of test staples 120 may then be automatically inspected utilizing the automated stapler inspection system 100 described herein to characterize performance of the stapler device 114 and associated cartridges 116.

The automated stapler inspection system 100 includes an imaging device 112, an inspection processing device 110, a user device 106, a machine learning (ML) training system 102, and a training image store 104, and a network 108. The imaging device 112 captures a sequence of images of the test skin 118 for processing by the inspection processing device

110. In one implementation, the imaging device 112 may comprise a digital microscope that captures video and/or still images of the test skin 118 from one or more perspectives. To accommodate capture of a test skin 118 that does not fit within a single frame of the imaging device 112 with sufficient resolution, the imaging device 112 may comprise a mechanically controlled imaging head that may be moved relative to the test skin 118 while capturing video that scans the length of the test skin 118 from one or more perspectives. Alternatively, the imaging device 112 may include a movable and/or rotatable fixture that secures the test skin 118 and is moved relative to a fixed imaging head to scan the length of the test skin 118 from one or more perspectives. Images of different sections of the test skin 118 may be extracted from captured video and processed through the inspection processing device 110 as will be described in further detail with respect to FIG. 2.

In other embodiments, the imaging device 112 may be designed with optics sufficient to capture the entire length of the test skin 118 in a single image with sufficient resolution to perform the automated inspection described herein. In yet further embodiments, the imaging device 112 may comprise a multicamera device that concurrently or sequentially captures images of different sections of the test skin 118 without necessarily requiring relative movement of the imaging device 112 and test skin 118 for scanning.

The inspection processing device 110 performs processing of the images and/or video captured from the imaging device 112 to generate automated inspection data characterizing the set of test staples 120. Furthermore, the inspection processing device 110 may identify or predict specific defects in the stapler device 114 and/or cartridges 116 based on the staple inspection data. The inspection processing device 110 may generate one or more reports comprising raw inspection data and/or various analytics derived from the raw inspection data. These reports may be viewable via one or more user devices 106 and/or may be employed to improve design and/or manufacturing of the stapler device 114 and/or cartridges 116.

In one implementation, the inspection processing device 110 applies one or more automated image processing algorithms to images obtained from the imaging device 112. The processing automatically characterizes aspects of the test staples 120 such as presence or absence of test staples 120 relative to an expected staple pattern, formation of test staples 120 (i.e., whether staples are properly formed or have one or more formation defects), staple heights of test staples 120, cutline length (for endocutter-type devices) or other inspection parameters. The image processing techniques may include application of one or more machine learning algorithms trained by the ML training system 102 as further described below.

The inspection processing device 110 may comprise a personal computer (desktop or laptop), tablet, mobile device, or console that enables inputs and outputs via the user device 106. In some embodiments, the inspection processing device 110 and user device 106 may be integrated (e.g., as a personal computer that performs functions of the inspection processing device 110 and user device 106). In other embodiments, the inspection processing device 110 and the user device 106 may be separate devices having independent computing resources (e.g., processors, storage, etc.). The inspection processing device 110 may be coupled to the imaging device 112 via a network 108 or directly connected to the imaging device 112. In some such embodiments, the inspection processing device 110 may be physically integrated with the imaging device 112. In any of these implementations, the machine learning models may be edge-deployed models of sufficiently small size to be executed on such an edge device that typically has limited computing and memory resources relative to large cloud computing systems.

In another embodiment, the inspection processing device 110 may comprise one or more on-site servers or a cloud computing system that is remote from the imaging device 112. For example, the inspection processing device 110 may include a distributed processing and storage system coupled over the network 108. In these embodiments, the inspection processing device 110 may receive video (or still images) from the imaging device 112 via the network 108, processing the images to generate inspection data, and output the inspection data to one or more user devices 106. In some such embodiments, the inspection processing device 110 and ML training system 102 (described below) may be integrated into a single system and/or may share certain processing modules common to both the training and inference processes.

The inspection processing device 110 may include a non-transitory computer-readable storage medium that stores instructions for execution by one or more processors to carry out functions described herein. In some implementations, the inspection processing device 110 may include a neural processing unit (NPU) specialized in performing machine learning inferences with high efficiency. Processing may also be performed using one or more general purpose processors (CPU) and/or graphics processing units (GPUs) instead of or in combination with one or more NPUs. The inspection processing device 110 may also include specialized hardware (e.g., an Application Specific Integrated Circuit (ASIC)) for performing at least some aspects of the processing described herein.

The machine learning (ML) training system 102 trains the one or more machine learning models applied by the inspection processing device 110 based on a set of training images stored to the training image store 104. The training images include images of test staples 120 deployed in test skins 118 that have been annotated to include labels characterizing the presence or absence of staples at each position of an expected staple pattern, a formation classification identifying one or more defects on a per-staple basis, and information characterizing locations of certain keypoints in the structure of each staple that may be used to derive respective staple heights. Annotations may be stored as metadata associated with images in the training image store 104. Examples of annotation techniques and training algorithms are described in further detail below with respect to FIGS. 3-6.

The ML training system 102 may furthermore apply one or more validation procedures to validate trained machine learning models prior to deployment. Validation results may be used to determine when a trained model is ready for deployment and may be used to optimize the training and/or inferences processes. Validation results may furthermore be useful to optimally scale down trained models to sizes that can be effectively deployed on an edge device.

Functions of the ML training system 102 described herein may be implemented as instructions stored to one or more non-transitory computer-readable storage mediums that are executed by one or more processors. The computing and storage components of the ML training system 102 and training image store 104 may include on-site computing or storage systems, cloud computing or storage systems, or a combination thereof and may be implemented utilizing local or cloud-based servers, which may include physical or virtual machines, or a combination thereof. Cloud-based servers may include private cloud systems, public cloud systems, hybrid public/private cloud systems, or a combination thereof. Accordingly, the ML training system 102 and training image store 104 may be local, remote, and/or distributed relative to the manufacturing and/or testing environments where the imaging device 112, inspection processing device 110, and/or user devices 106 operate. Furthermore, different portions of the ML training system 102 may execute on different remote servers and various system elements of the ML training system 102 and training image store 104 may be communicatively coupled over a network 108.

The training image store 104 stores training images used by the ML training system 102 to train the ML models. The training images may be derived from video or images of test staples 120 in test skins 118 captured from an imaging device 112 in the setup described above. To capture training images sufficient for training the ML models, the test setups may include test skins 118 under a variety of conditions. For example, the training set may include images of test skins 118 with and without missing staples 120, with different variations of well-formed staples 120 and defective staples 120, and with differently positioned cutlines. Furthermore, the training image set may include test staples 120 with varying staple heights and other characteristics (e.g., staple type, staple size, staple patterns, etc.), staples deployed from different types of stapler device 114, and staples deployed from different types of cartridges 116. The training image set may also include training images captured from a variety of different perspectives, lighting conditions, resolutions, fields of view, or other characteristics of the imaging device 112 and/or imaging setup. Training images may each depict only a portion of the length of a test skin 118 and do not necessarily capture the entire test skin 118 and associated staple pattern.

The user device 106 may include any input/output device for inputting information and/or control commands associated with inspection processing device 110, viewing various information, and/or interacting with various data. The user device 106 may operate one or more applications that include a user interface for performing various functions described herein. The application may comprise a web-based application accessible by a web browser or a locally installed application. The application may allow the user device 106 to facilitate functions such as controlling the imaging device 112 and/or inspection processing device 110, viewing, adding, removing, editing, or otherwise interacting with images obtained by the imaging device 112, initiating processes performed by the inspection processing device 110, and viewing outputs from the inspection processing device 110 such as inspection results, analytical data, recommendations, or various reports that may aggregate data into various visualizations such as charts, graphs, tables, etc. In one implementation, the user device 106 may include input/output hardware such as a display, input device (e.g., touch screen, keyboard, mouse, etc.) that interacts with the computing resources of the inspection processing device 110 as part of an integrated computing system (e.g., a mobile phone, a tablet, a laptop or desktop computer, or other computing device). Alternatively, the user device 106 may comprise a separate computing device from the inspection processing device 110. Here, the user device 106 may include conventional computer hardware such as a display, input device (e.g., touch screen), memory, a processor, and a non-transitory computer-readable storage medium that stores instructions for execution by the processor in order to execute the user interface application and carry out functions of the user device 106 described herein.

The network 108 comprises communication pathways that may enable communication between connected devices (such as one or more of the training image store 104, the ML training system 102, the user device 106, the imaging device 112, and the inspection processing device 110.) The network 108 may include one or more local area networks and/or one or more wide area networks (including the Internet). The network 108 may also include one or more direct wired or wireless connections (e.g., Ethernet, WiFi, cellular protocols, WiFi direct, Bluetooth, Universal Serial Bus (USB), or other communication link). In various configurations of the automated stapler inspection system 100, one or more of the elements 102, 104, 106, 110, 112 are not necessarily directly coupled to the network 108 and may instead only be locally connected. For example, the imaging device 112, user device 106, and the inspection processing device 110 may be directly coupled via a local link (or integrated into a single physical device) and do not necessarily have separate independent connections to the network 108. Moreover, some elements may be coupled only via a local area network while other elements may be coupled via a wide area network (such as the Internet). For example, in one implementation of the automated stapler inspection system 100, the imaging device 112, inspection processing device 110, and one or more user devices 106 may be locally connected via a local area network at a manufacturing and/or testing site, while the ML training system 102 and training image store 104 may be remote from the manufacturing and/or testing site and implemented via cloud computing datacenters accessible via a wide area network. In some embodiments, one or more components 102, 104, 106, 110, 112 may be isolated from the network 108. In such embodiments, data transfers may nevertheless occur via physical storage devices that can be manually transported. For example, images from an imaging device 112 could be transported and loaded to the inspection processing device 110 via a physical storage medium such as a disk drive, solid state drive, or other storage medium. Furthermore, models developed by the ML training system 102 may be manually loaded to the inspection processing device 110 via a memory card, USB storage device, or other portable storage medium without necessarily requiring network connectivity.

Figure 2:
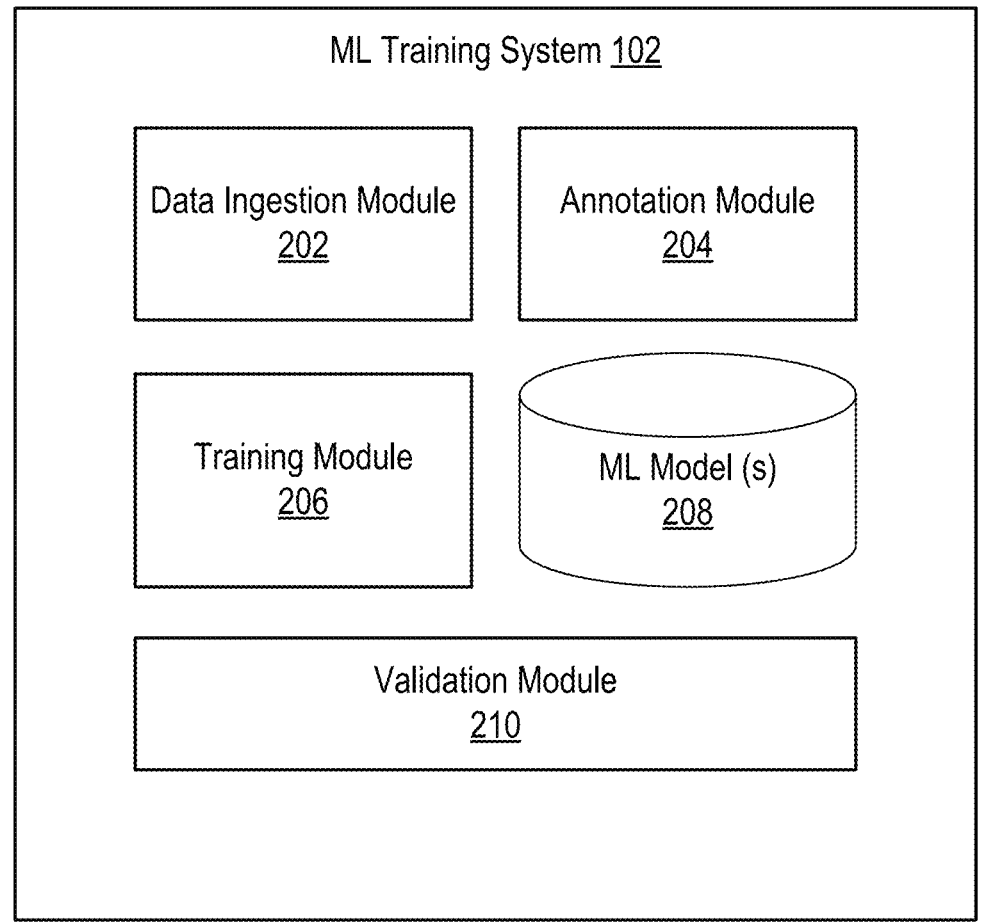
FIG. 2 is an example of a machine learning training system for training one or more machine learning models for automatically inferring inspection data from captured images.

FIG. 2 is a block diagram illustrating an example of an ML training system 102. The ML training system 102 may include a data ingestion module 202, an annotation module 204, a training module 206, an ML model store 208, and a validation module 210. In alternative embodiments, the ML training system 102 may include different or additional modules. Each of the modules 202, 204, 206, 208, 210 may be implemented using one or more non-transitory computer-readable storage mediums that instructions executable by one or more processors to carry out the functions attributed the respective modules 202, 204, 206, 208, 210 as described herein. The one or more processors and one or more storage mediums are not necessarily co-located and may be distributed (e.g., in a cloud architecture).

The data ingestion module 202 facilitates preprocessing of training images used by the training module 206 to train the one or more ML models. In one embodiment, the data ingestion module 202 may pre-process images from one or more images sources and store the preprocessed images to the training image store 104. Alternatively, the training image store 104 may store images that have not yet been fully preprocessed and the data ingestion module 202 may preprocess the images as they are retrieved from the training image store 104.

The data ingestion module 202 may perform preprocessing to transform images from a native image format (e.g., as may be output by the imaging device 112) into a standardized format. The standardized format may comprise a standard image size, encoding format, resolution, etc. The data ingestion module 202 may furthermore apply one or more filters to images or video to select images suitable for storing to the training image store 104. For example, the data ingestion module 202 may process video to extract a set of key frames that collectively depict the full length of the test skin 118 and may selectively discard other frames. Images may furthermore be filtered to detect and discard images that fail to meet certain quality criteria relating to image focus, contrast, brightness, occlusions, or other quality parameters.

The annotation module 204 facilitates obtaining annotations of the training images that become labels in the machine learning process. In one such embodiment, the annotation module 204 may generate a user interface accessible via a user device 106 that presents training images and enables an annotator to annotate the images with locations of test staples 120 (e.g., by drawing a bounding box around each respective staple 120) and labeling each staple 120 with a class descriptor relating to its formation. In one implementation, the class descriptors may be selected in a binary manner, for example as "good" or "bad" (alternatively, "pass" or "fail," "well-formed" or "defective," or any other binary label set). In another implementation, the class descriptors may include two or more classes of malformed staples. For example, possible descriptors could be selected from "good," or a set of "bad" classes including "left leg malformed," "right leg malformed," or "both legs malformed." Furthermore, the set of classes could include two more "good" classes corresponding to different structural variations that are each acceptable. Examples of labels associated with staple locations and examples of possible classes are described in further detail below with respect to FIGS. 4-5.

The annotation module 204 may furthermore facilitate obtaining annotations that mark certain keypoints in the staple structure, from which staple height may be calculated. For example, the user interface of the annotation module 204 may request that the annotator click on a set of specified keypoints on each detected staple, such as the peak points of each looped leg, points on the crown where the legs begin to bend, or other specified structural landmarks. Examples of specific keypoints are described in further detail below with respect to FIG. 4.

The training module 206 executes one or more machine learning algorithms to train one or more machine learning models based on the training images and corresponding annotations. These machine learning algorithms generally operate to generate and iteratively update a set of model parameters (e.g., weights) in a supervised learning process that collectively characterize the statistical relationships between the set of training images and the annotations. In one implementation, the training module 206 trains two independent machine learning models: an object detection and classification model trained to detect staples and classify their formation, and a keypoint detection model trained to detect certain keypoints in the staple structures. The training process is further described below with respect to FIG. 6.

The validation module 210 may perform validation of the one or more machine learning models. In the validation process, a model may be applied to a labeled test image to generate inferences, and the inferences may be compared to ground truth data to characterize performance of the models. Validation results may be assessed at various iterations of the training process to determine when a sufficient number of iterations have been executed to achieve a desired performance level. Ground truth data for the object detection and classification model may be directly derived from the labels for the test images. For the keypoint detection model, staple heights may be computed from the inferred keypoint locations and compared to ground truth staple height data derived from manufacturer specifications or direct staple measurements.

The model store 208 stores the one or more machine learning models generated by the training module 206. The model store 208 may be accessed by the inspection processing device 110 to enable the automated inspection process described herein.

Figure 3:
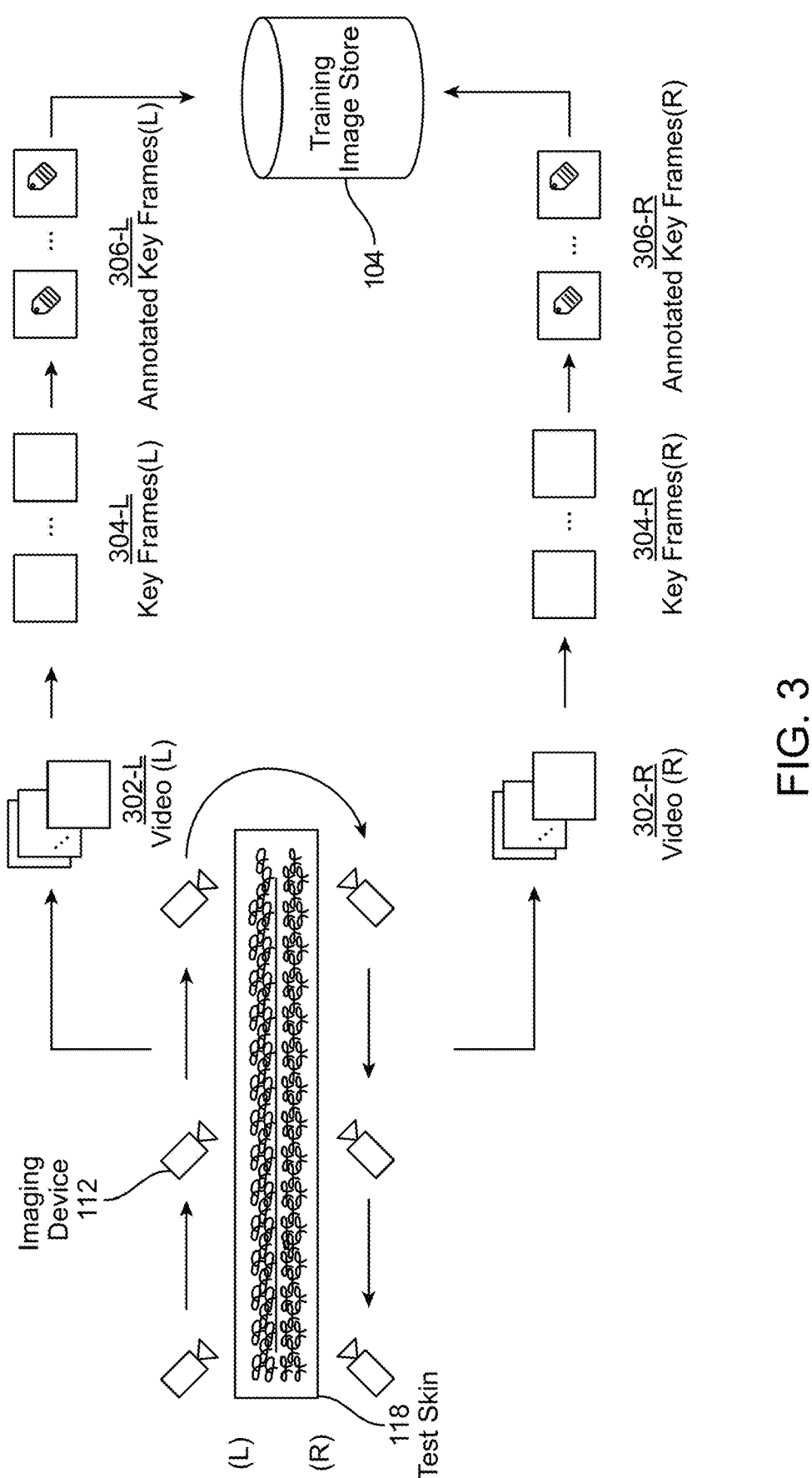
FIG. 3 is an example embodiment of an image capture and processing setup for capturing images of a test skin and corresponding set of test staples, and for obtaining annotations for the images.

FIG. 3 illustrates an example embodiment of a process for obtaining annotated training images for storing to the training image store 104. In this example, a test skin 118 with deployed test staples 120 is placed in a fixture that holds the test skin 118 in place for scanning by the imaging device 112. The imaging device 112 first scans the test skin 118 from a first perspective (e.g., at an approximately 45 degree elevational angle from a left side of the test skin 118). The imaging device 112 then scans the test skin 118 from a second perspective (e.g., at an approximately 45 degree elevational angle form a right side of the test skin 118). The imaging device captures video (i.e. a sequence of image frames) as it scans, with each video frame capturing a portion of the test skin 118 within the current field of view. This results in a left perspective video 302-L and right perspective video 302-R of the full length of the test skin 118.

Each of the left perspective video 302-L and right perspective video 302-R may be processed to extract a set of left perspective key frames 304-L and right perspective key frames 304-R respectively. The key frames 304-L, 304-R may represent a reduced image set that collectively depicts the entire test skin 118 from each of the left and right perspectives. In an embodiment, the start time of the video and motion of the imaging device 112 may be precisely controlled in a consistent manner such that the key frames 304 may correspond to the same set of predefined frame indices in each video capture. Alternatively, various image processing techniques may be to derive the key frames 304 (e.g., based on identifying frames with predefined overlap at their edges).

The key frames 304-L, 304-R may be provided to the annotation module 204 to obtain annotations as described above. In one embodiment, for ease of annotation, the respective sets of left key frames 304-L and right key frames 304-R may each be stitched together to generate respective left and right composite images of the entire test skin 118 for presenting to annotator. Annotations may then be stored in association with the individual frames to which they correspond. In another embodiment, the key frames 304-L, 304-R may be individually presented to the annotator without necessarily performing any image stitching. Annotations may be stored as metadata associated with the respective key frames 304-L, 304-R. Both the images and annotations may be stored to the training image store 104.

As described above, the left and right perspective videos 302-L, 302-R may be captured from a microscope setup in which a movable and rotatable imaging head captures video while moving along a track on one side of the test skin 118, and then rotates and moves back along the track to capture video from the second side of the test skin 118. However, in alternative setups, equivalent video may be captured by rotating and moving the test skin 118 relative to a fixed imaging head. In other setups, key frames 304-L, 304-R may be captured directly from one or more cameras either by moving the imaging head to appropriate positions for capturing individual images, by using a multicamera setup, or by using optics suitable for capturing the whole length of the test skin 118 and digitally splitting the captured image.

Figure 4:
FIG. 4 is an example annotated image of a set of test staples that may be included in a training dataset for training the one or more machine learning models.
Figure 4:
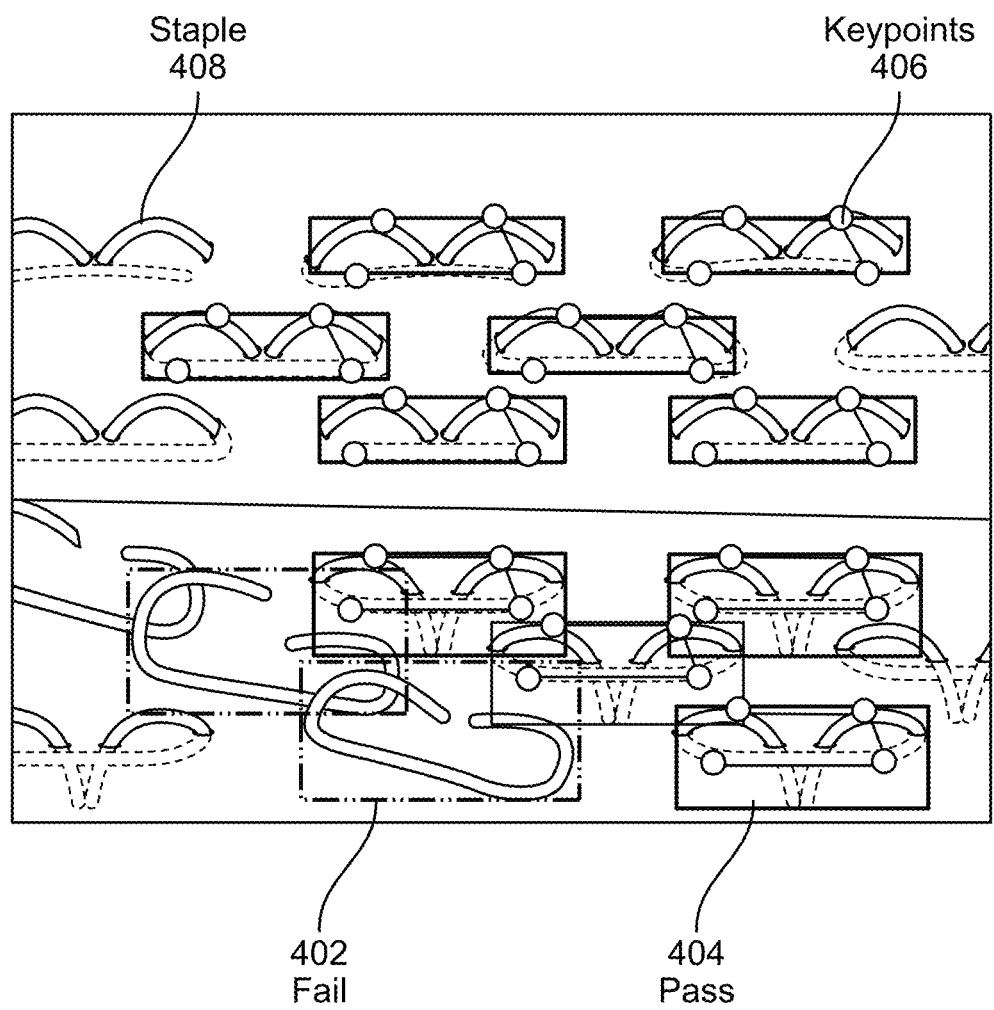

FIG. 4 illustrates a visual representation of an annotated training image 400 as it may appear in an annotation interface for obtaining annotations from an annotator. The training image shows a portion of a test skin 118 with a set of deployed staples 408. In this example illustration, the solid line portions of the staples 408 indicate portions above the upper surface of the test skin 118 while the dashed line portions indicate visible portions of the staple 408 below the upper surface of the test skin 118. Portions of the staples 408 below the surface of the test skin 118 may be hidden from view in some instances, depending on the nature of the test skin 118, staple characteristics, perspective of the imaging device 112, or other variables.

The staples 408 are annotated with respective bounding boxes 402, 404 that represent the boundaries of each staple 408 as determined by the annotator. Different styles of bounding boxes may indicate different class descriptors. In this example, the annotator applies a binary classification scheme in which the form of the staples 408 may be labeled as either "pass" 404 or "fail" 402.

The annotations also include a set of keypoints 406 per staple 408 that indicate locations of a predefined set of structural features as determined by the annotator. In one embodiment, each staple 408 is labeled with four keypoints 406: two keypoints that indicate respective locations of the peaks of each staple leg (i.e., highest points of each staple 408) and two keypoints on the crown representing points on each side where the staple begins to bend upwards. Keypoints 406 need not be provided for malformed staples (e.g., staples 408 labeled as "fail" 402).

In practice, the annotations may be obtained via an annotator user interface via a user device 106 that provides tools enabling the annotator to directly draw bounding boxes, select class labels, and mark the keypoints. The annotations may be stored as numerical and/or text-based metadata defining the bounding box locations, class assignments, and keypoint locations.

Figure 5:
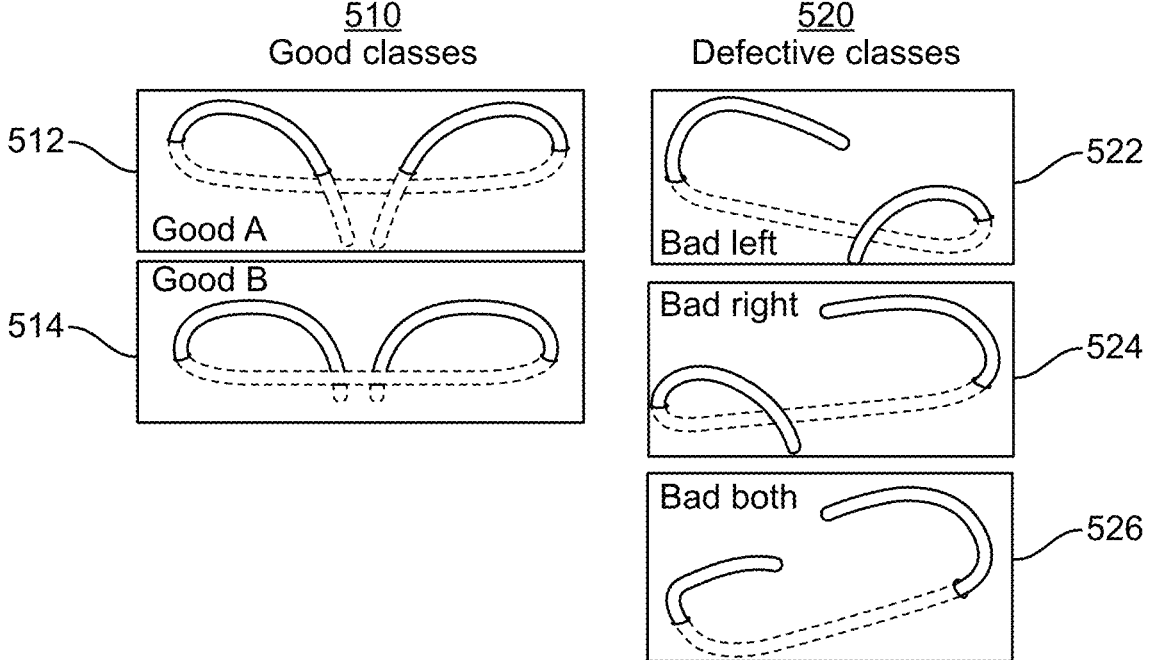
FIG. 5 is a set of example images of staples corresponding to different formation classes that may be automatically detected by the one or more machine learning models.

FIG. 5 illustrate additional examples staple images and corresponding class labels that may be used embodiments employing a multi-class object classifier. In this example, the general classes include "good" classes 510 in which the staple 408 is deemed well-formed and a set of "defective" classes 520 in which the staple 408 has one or more malformations. The "good" classes may include a "good A" class 512 in which the staple legs are bent to cross in front of the crown, and a "good B" class 514 in which the staple legs are bent behind the crown. In both cases, the staple legs are fully looped around to cross the plane of the crown, thus enabling the staples to fully seal tissue. The "defective" class may include a "bad left" class 522 in which the left leg (only) of the staple is malformed, a "bad right" class 524 in which the right leg (only) of the staple is malformed, and a "bad both" class 526 in which both the left and right legs of the staple are malformed. In each of the defective classes 520, one or more legs of the staple are not fully bent into place and do not cross the plane of the crown. Such malformed staples may fail to seal tissue.

As described above, one implementation of the machine learning system 102 and the inspection processing device 110 does not distinguish between different classes of "good" 510 and "bad" 520 staples (although all variations may be included in the training image store 104 for training processes). In this implementation, the object detection and classification model may be trained as a binary classifier. In another embodiment, the machine learning system 102 may train a multi-class classifier trained to distinguish between the more specific classes 512, 514, 522, 524, 526. In other embodiments, different classification schemes may be employed depending on the desired level of classification granularity and the types of malformations sought to be detected.

Figure 6:
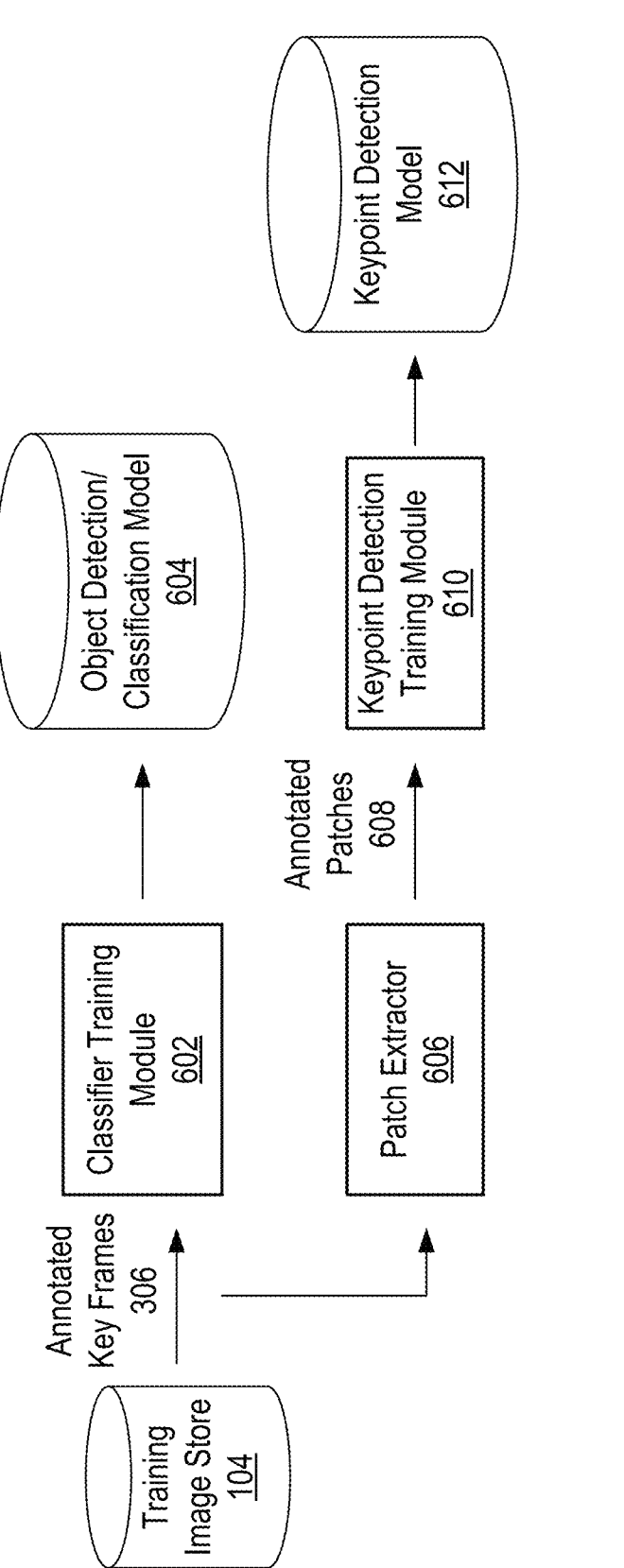
FIG. 6 is an example implementation of a machine learning training system.

FIG. 6 illustrates an example implementation of an ML training system 102. In a first training path, a classifier training module 602 applies a classification training algorithm to annotated key frames 306 in the training image store 104 to train an object detection and classification model 604 for detecting and classifying staples 120 of a test skin 118. Training may be performed in an offline manner using a sufficient number of training images from the training image store 104 and employing a sufficient number of training iterations to achieve desired performance characteristics. In one implementation, the object detection and classification model 604 may comprise a "You Only Look Once" (YOLO) variant of a convolutional neural network (CNN). In other implementations, the object detection model may comprise a different type of CNN, or other type deep learning network.

A patch extractor 606 generates a set of image patches 608 corresponding to individual staples as identified by the bounding box annotations in the annotated key frames 306. The image patches 608 may be limited to those labeled as "good" in the annotated key frames 306. A keypoint detection training module 610 applies a model training algorithm to the annotated patches 608 to generate a keypoint detection model 612 for detecting the locations of keypoints. The keypoint detection model may comprise Vision Transformer Pose Estimation (ViT Pose) model in one implementation. In other variations, the keypoint detection model may comprise a different type of Vision Transformer or pose estimation model, or another type of deep learning network.

Figure 7:
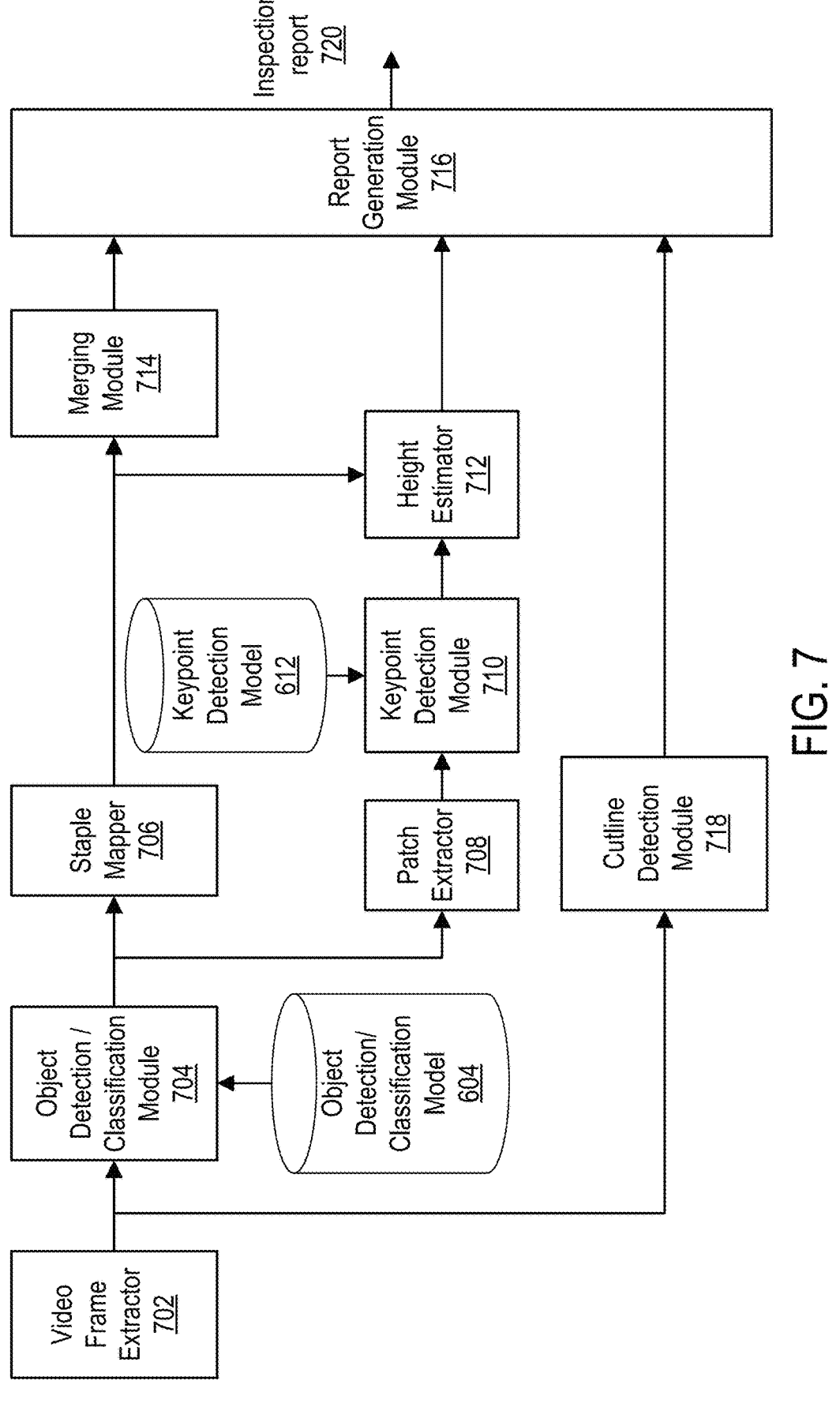
FIG. 7 is an example implementation of an inspection processing device.

FIG. 7 illustrates an example implementation of an inspection processing device 110. A video frame extractor 702 receives video from an imaging device 112 depicting a test skin 118 under inspection and extracts a set of key frames for processing. The imaging device 112 and video frame extractor 702 may employ the same techniques described above with respect to FIG. 3 to capture video 302-L, 302-R from left and right perspectives and extract left and right key frames 304-L, 304-R. An object detection and classification module 704 applies the trained object detection and classification model 604 in an inference process to infer locations and classify formation of staples 120 in a test skin 118 under inspection. The inferred locations may be defined by bounding boxes that bound respective staples 120. Inferences may also include confidence scores indicating confidence levels of the inferred results.

The staple mapper 706 maps each detected staple to a staple identifier uniquely corresponding to a specific staple location of an expected staple pattern. The expected staple pattern may include a predefined number of staples organized into an expected number of rows, an expected number of staplers in the respective rows, and expected positions of individual staples in each row. Because video is captured from both left and right perspectives, the staple mapper 706 may generate two separate maps of detected staple positions and classifications (one derived from the left perspective images and one derived from the right perspective images).

For each key frame 304, the staple mapper 706 may map the location of the bounding box from a frame-specific coordinate system to a global coordinate system characterizing the full test skin 118. In one embodiment, a set of fiducial markers on the fixture that holds the test skin 118 may aid transformation. Alternatively, the mapping may be performed using various imaging processing techniques that do not necessarily rely on fiducial markers. This mapping results in constructing a left map derived from staples detected in left-perspective key frames 304-L and a right map derived from staples detected in the right-perspective key frames 304-R. Each map reflects the inferred staple positions in the global coordinate system. Row and column detections may then be performed on each map to map the inferred positions into nearest rows and columns consistent with the expected staple pattern. Based on the row and column detections, the detected staples may be mapped to unique staple identifiers (for each of the left map and right map) that are consistent with the row and column locations in the expected staple pattern. Missing staples may be identified where no staple is detected corresponding to a staple identifier in the expected staple pattern.

The merging module 714 merges the objection detection and classification results from the left and the right maps into a single detection and classification map. The merging module 714 may apply a set of predefined rules to resolve discrepancies between the left and right map. In one example, the merging module 714 classifies a staple according to the classification result from the left and right staple maps having the higher confidence classification. If a staple is detected in one map and missing in another map, the classification in the map where the staple was detected may be carried forward. In another implementation, the merged classification of a staple may "bad" if the staple is classified as "bad" in either the left or right map regardless of the confidence levels.

In another processing path, a patch extractor 708 generates image patches for each detected staple using the bounding boxes detected by the object detection and classification module 704. In one implementation, the patch extractor 708 may process only "good" staples and ignore staples classified as being malformed. A keypoint detection module 710 then applies the keypoint detection model 612 to the respective image patches to infer keypoint locations for each detected staple. The keypoints per patch may be transformed into a universal coordinate system for the full test skin 118. In an embodiment, fiducial markers on the fixture holding the test skin 118 may aid in this transformation as described above.

The height estimator 712 calculates a height of each staple (and/or individual staple legs) based on the detected keypoint locations. The heights may be calculated as follows:

$$H = \frac{\sqrt{HL^2 + HR^2 + 2HL * HR * \cos\alpha}}{\sin\alpha}$$

where H is the height of a staple or individual staple leg, HL is a pixelwise height estimate from a left perspective view of the staple, HR is a pixelwise height estimate from a right perspective view of the staple, and a is a parameter representing the angle between the left and right view directions. The pixelwise heights HR, HL may be determined from the pixel counts between the left crown and left peak and pixel counts between the right crown and right peak. This computation may be performed separately for the left and right legs, or the heights may be averaged (or otherwise combined) to generate a single height value per staple. The pixelwise height estimates HL, HR corresponding to the same staple may be determined using the staple maps derived from the staple mapper 706 described above.

A cutline detection module 718 may detect a location of the cutline (For endocutter-type stapler devices 114) using various classical computer vision techniques. For example, cutline detection may be performed using a sequence of techniques such as adaptive thresholding, Top Hat and Close kernels, and contour detection (e.g., based on empirically determined height thresholds). Cutline detection may be performed separately on each side and the minimum measured distance may be computed as the final estimated cutline length. For stapler devices 114 that do not perform cutting, the cutline detection module 718 may be omitted.

A report generation module 716 may generate one or more inspection reports 720 based on results of the merged object detection and classification (from the merging module 714), the estimated staple heights (from the height estimator 712), and the estimated cutline length (from the cutline detection module 718). Examples of reports are illustrated in further detail below with respect to FIGS. 11-12.

Figure 8:
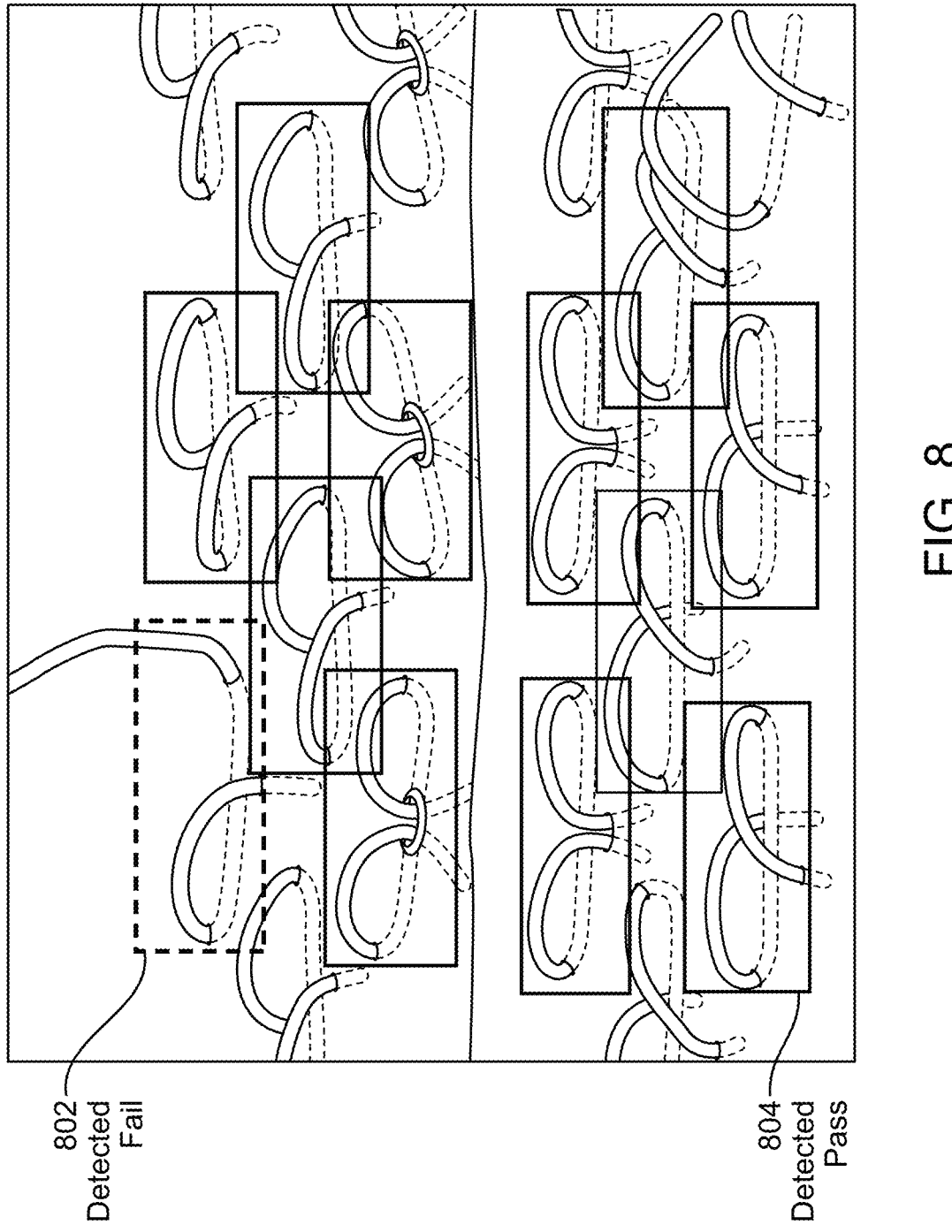
FIG. 8 is an example image representing inferred locations and classes of staples resulting from application of an object detection and classification model.
Figure 9:
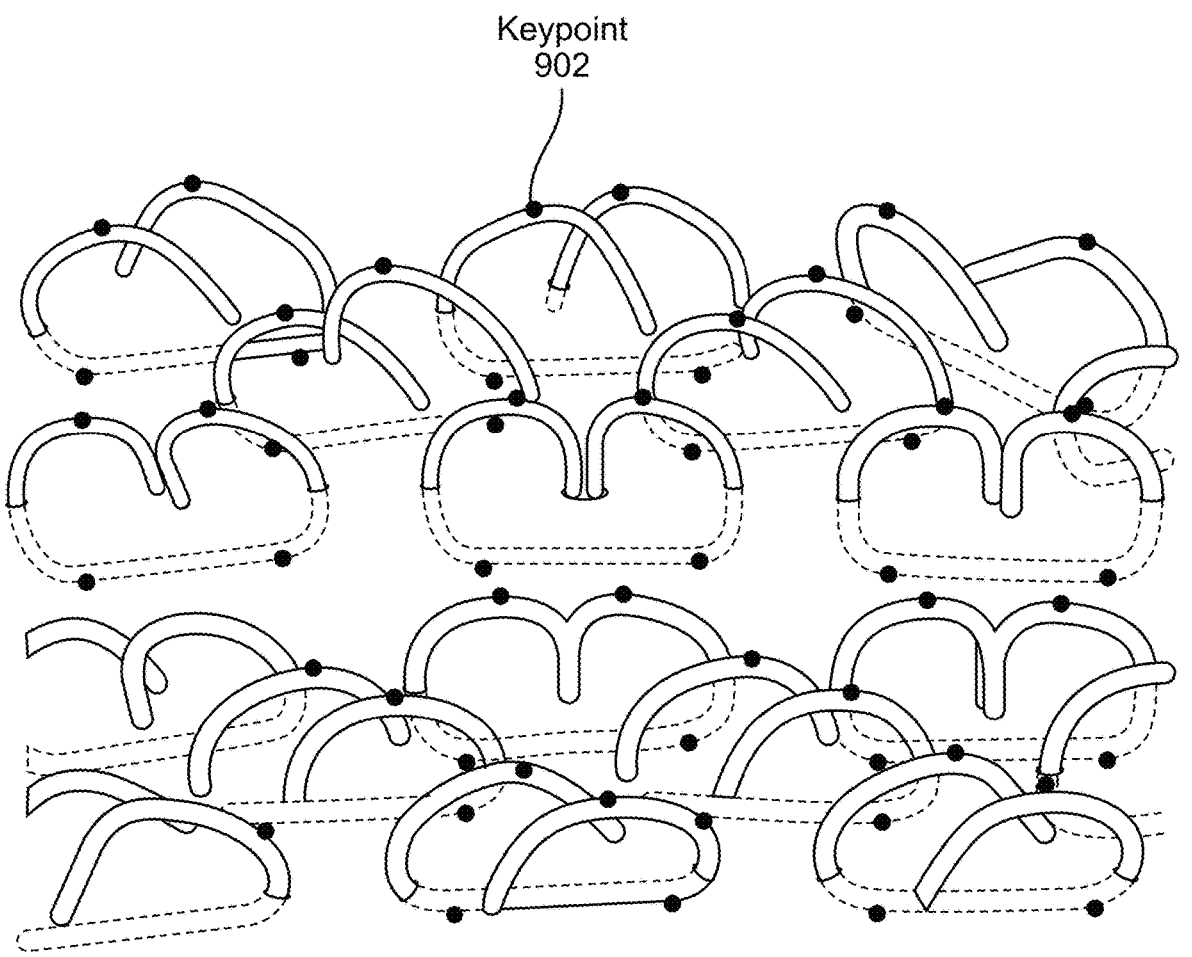
FIG. 9 is an example image representing inferred keypoints of staples resulting from application of a keypoint detection model.
Figure 10:
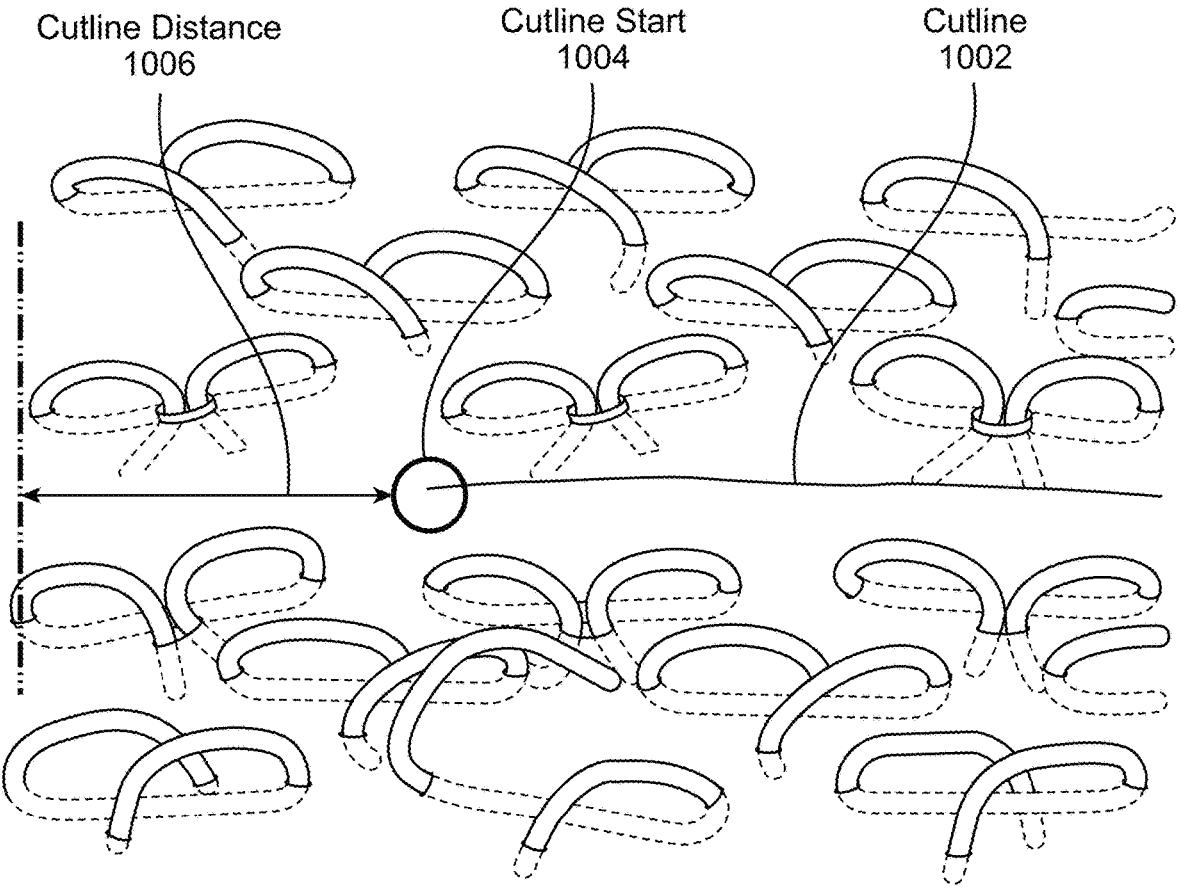
FIG. 10 is an example image representing an automated detection of a cutline length.

FIG. 8-10 are example visualizations illustrating detection results determined by the inspection processing device 110 with respect to a sample key frame. FIG. 8 shows an object detection and classification result. In this example, locations of detected staples are indicated by bounding boxes 802, 804 where "good" staples are indicated by a solid-line bounding box 804 and "bad" staples are indicated by a dashed line bounding box 802. FIG. 9 illustrates a keypoint detection result for the sample key frame. Locations of detected keypoints 902 are plotted per staple. FIG. 10 shows a cutline estimation result for the sample key frame. Here the cutline start location 1004 is determined from the detected cutline 1002 and a cutline distance 1006 between the edge of the staple rows and the cutline start location 1004 may be computed. These types of visualizations may be included in a report accessible via a user device 106.

Figure 11:
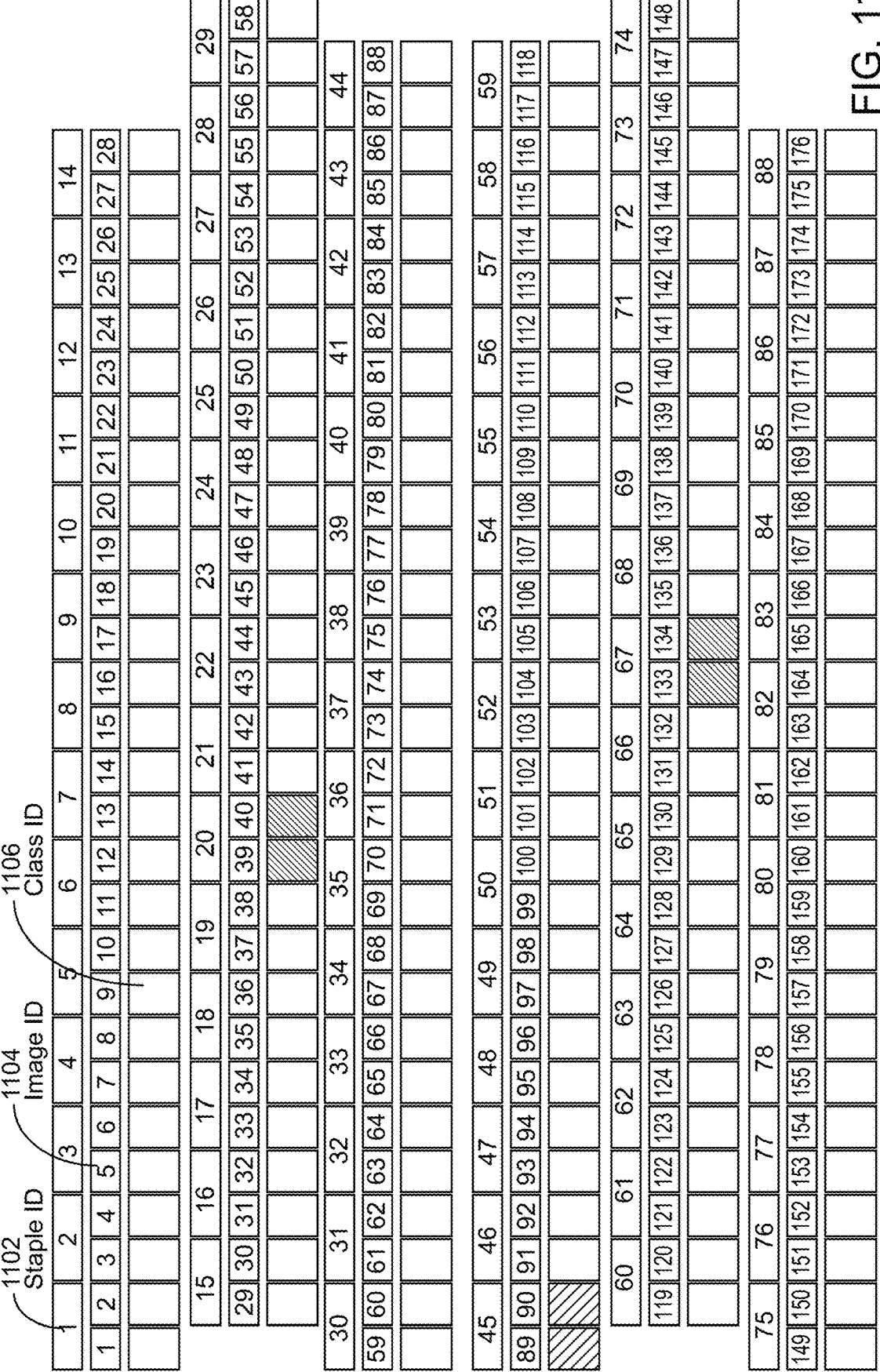
FIG. 11 is a first example of inspection data that may be included in a digital report generated by an automated stapler inspection system.

FIG. 11 is an example chart for an inspection report representing classification results for a test skin 118 under inspection. The chart shows a staple pattern with each staple position represented by a unique staple identifier 1102. Each staple identifier 1102 is further associated with a pair of image identifiers 1104 corresponding to the left and right perspective images used for classification of each staple position. The class identifiers 1106 represent a classification result for each image identifier 1104. In this example, a binary classification is used in which unshaded boxes represented a "good" class identifier 1106, the densely shaded boxes represent a "bad" class identifier 1106 (e.g., as shown in image IDs 39, 40, 133, 134 in this example), and the lightly shaded boxes indicate missing staples (e.g., as shown in image IDs 89, 90 in this example). In other implementations, the pair of class identifiers 1106 for each stapler identifier 1102 may be resolved to a single classification based on a set of classification rules (e.g., by classifying the staple as "bad" if either the left or right image classification indicates a bad staple).

FIG. 12 is an example chart for an inspection report 720 representing staple height estimation results for a test skin 118 under inspection. Similar to FIG. 11, the chart shows a staple pattern with each staple position represented by a unique staple identifier 1202. Each staple identifier 1202 is associated with a pair of leg identifiers 1204 corresponding to the two respective legs of each staple. The height estimates 1206 indicate the estimated heights of the left and right legs respectively per staple. Height estimates 1206 are omitted for staples that are missing or malformed. In other implementations, the pair of heights for the left and right legs may be resolved to a single height per staple as discussed above.

Figure 13:
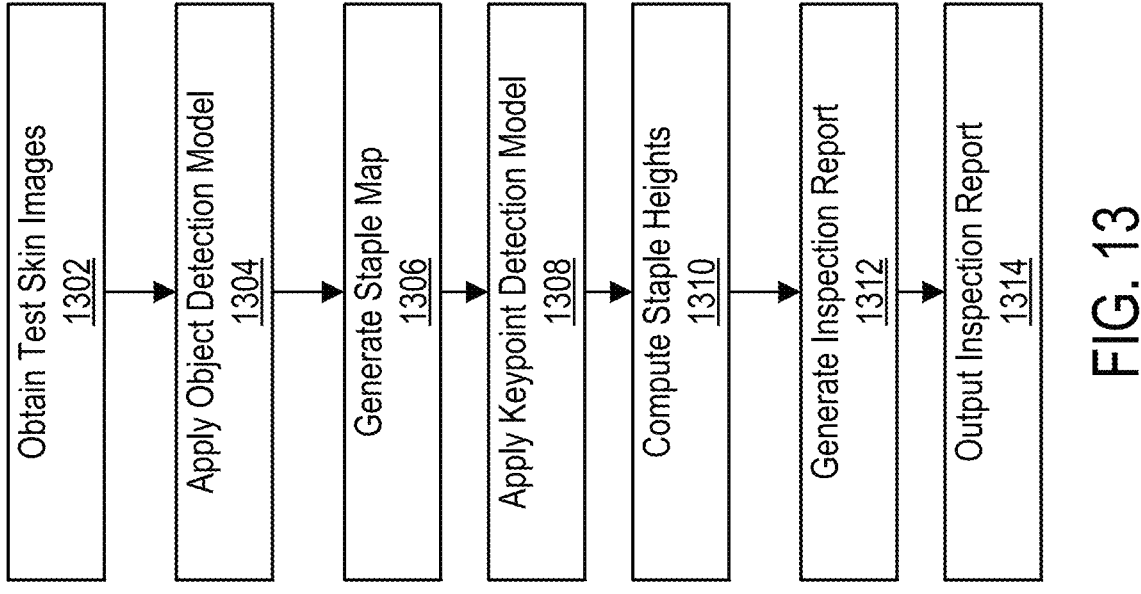
FIG. 13 is a flowchart illustrating an example embodiment of a process performed by the automated stapler inspection system.

FIG. 13 is a flowchart illustrating an example embodiment of a process for automatically inspecting surgical staples 120 fired into a test skin 118 by a stapler device 114. An inspection processing device 110 obtains 1302, from an imaging device 112, one or more images of the test skin 118 including the surgical staples 120. The set of images may include a left-side subset of images of the test skin 118 captured from a left side perspective view and a right-side subset of images of the test skin 118 captured from a right side perspective view. The inspection processing device 110 applies 1304 an object detection and classification model 604 to the one or more images to infer respective locations of the surgical staples and infer the respective classes of the surgical staples. The classes may include at least one class of defectively formed staples and at least one class of properly formed staples. In some implementations a binary classification may be employed. In another implementation, the defective classes may include, for example, a first class associated with a defectively formed left staple leg, a second class associated with a defectively formed right staple leg, and a third class associated with a defectively formed right staple leg. The inspection processing device 110 derives 1306 a staple map by mapping the respective locations to respective staple positions in an expected staple pattern and associating the respective classes with the respective locations. Generating the staple map may include generating a left staple map derived from the left-side subset of images, generating a right staple map derived from the right-side subset of images, and merging the left staple map and the right staple map to resolve discrepancies according to a predefined set of merging rules.

The inspection processing device 110 applies 1308 a keypoint detection model to the one or more images to infer locations of a set of keypoints of the surgical staples. The keypoints may include, for example, a first peak of a first formed staple leg, a second peak of a second formed staple leg, a first crown point on a crown below the first peak (where the crown begins to bend), and a second crown point on the crown below the second peak (where the crown begins to bend). The inspection processing device 110 computes 1310 respective staple heights for each of the surgical staples based on the locations of the set of keypoints. The inspection processing device 110 generates 1312 a digital inspection report based on inspection data including the staple map, the respective classes of the surgical staples, and the respective staple heights of the surgical staples. The digital report may be output 1314 to a user interface of a user device 106.

For endocutter-type stapler devices, the inspection processing device 110 may also detect a location of a cutline associated with the surgical staples and include information about the cutline location in the digital report.

Figure 14:
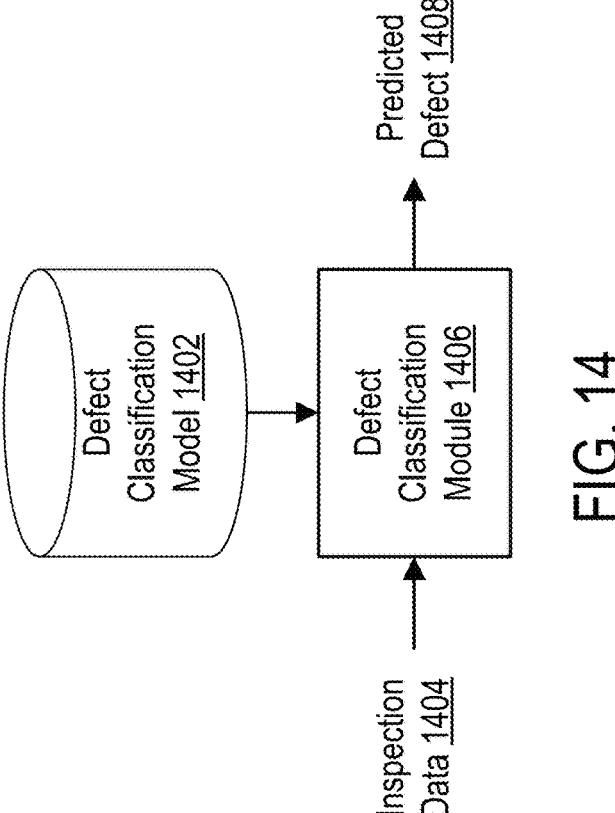
FIG. 14 is an example embodiment of defect detection module for automatically inferring defects in a stapler device or cartridge based on inspection data.

In further embodiments, the automatically derived inspection data from a set of staple tests may be used as inputs to train additional machine learning models. As one example, FIG. 14 illustrates an example embodiment of a defect classification module 1406 (which may be implemented in the user device 106, inspection processing device 110, or elsewhere). The defect classification module 1406 obtains the inspection data 1404 (e.g., as a feature vector) and applies a defect classification model 1402 to infer likelihoods of one or more classes of defects in the stapler device 114 or stapler cartridge 116. Examples of defect classes may relate to one or more defective components (e.g., a mis-sized component, a mis-shaped component, material defects, etc.), defects in assembly, incompatibilities between cartridges 116 and stapler devices 114, or other defects leading to a defective stapler pattern. The likelihood values for the respective defect classes may be directly provided in a report, or one or more recommendations may be generated based on the defect likelihoods.

The defect classification model 1402 may comprise a CNN or other machine learning network trained in a training process based on training data derived from historical staple tests. The training data may include, for each staple test, the resulting inspection datasets (e.g., staple detection data, staple classification data, staple height data, cutline location data, etc.) labeled based on defects (or lack thereof) in the stapler device 114 or cartridges 116 used in the test. Through the learning process, the defect classification model 1402 learns statistical correlations between patterns in the inspection data and defects (or lack thereof) in the stapler devices 114 and cartridges 116. Once trained, the model 1402 can generate predictions about what defects are present based on observed inspection data. In alternative embodiments, the defect classification model 1402 may apply one or more rule-based algorithms (instead of or in addition to machine learning techniques) to identify and classify defects based on patterns in the staple inspection data.

Figure 15:
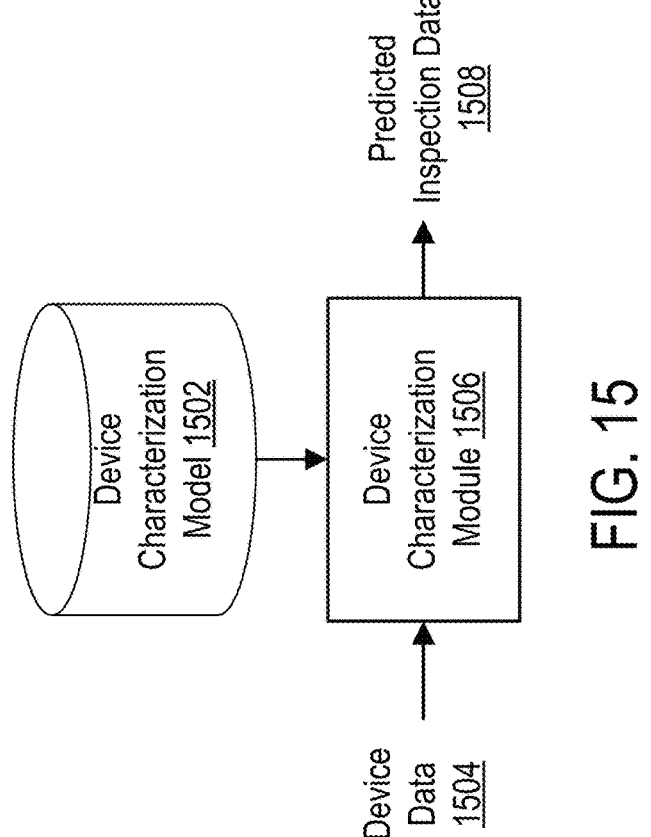
FIG. 15 is an example embodiment of a device characterization model for automatically inferring inspection data based on design parameters of a stapler device and/or stapler cartridge.

In a further embodiment as shown in FIG. 15, a device characterization model 1502 may be trained to map a set of device parameter data 1504 (e.g., component sizes, component shapes, component types, component materials, assembly methods, etc.) for stapler devices 114 and/or cartridges 116 to a set of predicted inspection data 1508 (e.g., likelihoods of misfired staples, likelihoods of malformed staples of one or more classes, likelihoods of different staple heights, etc.). The device characterization model 1502 may be applied to measured or otherwise specified parameters of a device to infer performance without directly testing the device. In one application, the device characterization model 1502 may be employed to model how proposed design changes are predicted to affect performance. Similarly, the device characterization model can model how different types of cartridges (having staples of varying thickness, height, material, or other parameters), may perform in combination with different variations of stapler device 114 without necessarily executing physical tests on each combination.

The device characterization model 1502 may comprise a CNN or other machine learning network trained in a training process based on training data derived from historical staple tests. The training data may include design parameters associated with stapler devices 114, cartridges 116, staples, or components thereof and corresponding inspection datasets from staple tests associated with historical tests of those devices. Through the learning process, the device characterization model 1502 learns statistical correlations between different design parameters and resulting inspection data. Once trained, the model 1502 can predict inspection data from the design specification, thus enabling tests to be simulated for different design characteristics.

The above-described system and methods may be utilized to automatically and rapidly perform inspection of test staple patterns for characterizing performance of a surgical stapling device. The described system and methods represent numerous technical improvements in various technical fields. For example, the described systems and methods provide technical improvements in the fields of device manufacturing, testing, and inspection because the disclosed system enables testing to occur rapidly, with finer-grained detail, with greater precision, and more autonomously than conventional manual inspection processes. Rather than relying on human observers that are typically limited to pass/fail results for the full staple test, the disclosed embodiments enable generating fine-grained inspection data described herein. These results are furthermore more consistent and objective than manual inspection techniques. The technical improvements in the testing process also directly lead to technical improvements in the devices themselves because defects can be rapidly detected and corrected.

The described systems and methods furthermore provide technical improvements in the fields of image processing, computer vision, and machine learning. For example, conventional object detection and classification techniques are not sufficiently tuned for the specific problem of detecting surgical staples, classifying their formation structures, and estimating staple heights. The described techniques employ a combination of different machine learning models (e.g., objection detection and classification model and a keypoint detection model) in combination with other specific processing steps to provide improved accuracy and precision. Furthermore, combining these two types of models in this way enables execution on an edge device, which may utilize lower network bandwidth, reduce computational resources, and provide greater data security than cloud-based solutions using conventional techniques.

The described systems and methods also provide a technical improvement in the field of medical treatment methods. The improved inspection process described above results in devices with lower rates of misfired staples, malformed staples, or improper staple heights, which ultimately yield better outcomes for surgical patients relative to procedures using devices reliant only on conventional inspection techniques.

The foregoing description of the embodiments has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe the embodiments in terms of algorithms and symbolic representations of operations on information. These operations, while described functionally, computationally, or logically, may be implemented by computer programs or equivalent electrical circuits, microcode, or the like. The described operations and their associated modules may be embodied in software, firmware, hardware, or any combinations thereof.

Any of the steps, operations, or processes described herein may be performed or implemented with one or more hardware or software modules, alone or in combination with other devices. Embodiments may also relate to an apparatus for performing the operations herein. This apparatus may be specially constructed for the required purposes, and/or it may include a general-purpose computing device selectively activated or reconfigured by a computer program stored in the computer. Such a computer program may be stored in a tangible non-transitory computer readable storage medium or any type of media suitable for storing electronic instructions and coupled to a computer system bus. Furthermore, any computing systems referred to in the specification may include a single processor or may include architectures employing multiple processor designs for increased computing capability.

Finally, the language used in the specification has been principally selected for readability and instructional purposes, and it may not have been selected to delineate or circumscribe the inventive subject matter. It is therefore intended that the scope is not limited by this detailed description, but rather by any claims that issue on an application based hereon. Accordingly, the disclosure of the embodiments is intended to be illustrative, but not limiting, of the scope of the invention, which is set forth in the following claims.

The invention claimed is:

1. A method for automatically inspecting surgical staples fired into a test skin by a surgical stapler, the method comprising:

obtaining, from an imaging device, one or more images of the test skin including the surgical staples;

applying an object detection model to the one or more images to infer respective locations of the surgical staples and infer respective classes of the surgical staples, wherein the object detection model is trained from a set of training images according to a first machine learning process;

mapping the respective locations to respective staple positions in an expected staple pattern and associating the respective classes with the respective locations to derive a staple map;

applying a keypoint detection model to the one or more images to infer locations of a set of keypoints of the surgical staples, wherein the keypoint detection model is trained from the set of training images according to a second machine learning process;

computing respective staple heights for each of the surgical staples based on the locations of the set of keypoints;

generating a digital inspection report based on inspection data including the staple map, the respective classes of the surgical staples, and the respective staple heights of the surgical staples; and outputting the digital inspection report to a user interface of a user device.

2. The method of claim 1, further comprising:

detecting, based on the one or more images, a location of a cutline associated with the surgical staples; and wherein the digital inspection report is further based on the location of the cutline.

3. The method of claim 1, wherein the respective classes of the surgical staples are selected from at least one class of defectively formed staples and at least one class of properly formed staples.

4. The method of claim 3, wherein the at least one class of defectively formed staples included a first class associated with a defectively formed left staple leg, a second class associated with a defectively formed right staple leg, and a third class associated with a defectively formed right staple leg.

5. The method of claim 1, wherein the set of keypoints includes a first peak of a first formed staple leg, a second peak of a second formed staple leg, a first crown point on a crown below the first peak, and a second crown point on the crown below the second peak.

6. The method of claim 1, wherein the one or more images includes a left-side subset of images of the test skin captured from a left side perspective view and a right-side subset of images of the test skin captured from a right side perspective view.

7. The method of claim 6, wherein deriving the staple map comprises:

generating a left staple map derived from the left-side subset of images;

generating a right staple map derived from the right-side subset of images; and merging the left staple map and the right staple map to resolve discrepancies according to a predefined set of merging rules.

8. The method of claim 1, further comprising:

obtaining a defect classification model trained in a third machine learning process;

applying the defect classification model to at least a subset of the inspection data to infer one or more classes of defects in the surgical stapler or cartridge from which the surgical stapler fires the surgical staples; and wherein the digital inspection report further identifies the one or more classes of defects.

9. The method of claim 1, further comprising:

obtaining a set of design parameters for the surgical stapler and a cartridge from which the surgical stapler fires the surgical staples;

storing the inspection data in association with a set of design parameters relating to the surgical stapler in a device model training dataset for training a device characterization model;

applying a machine learning process to train the device characterization model based on the device model training set; and obtaining input design parameters for a modified surgical stapler; and applying the device characterization model to the input design parameters to infer a set of inferred inspection data for the modified surgical stapler.

10. The method of claim 1, wherein applying the objection detection model and applying the keypoint detection model are carried out on an inspection processing device locally connected to the imaging device.

11. The method of claim 1, wherein the imaging device comprises a microscope with a movable and rotatable imaging head.

12. A non-transitory computer-readable storage medium storing instructions for automatically inspecting surgical staples fired into a test skin by a surgical stapler, the instructions when executed causing one or more processors to perform steps comprising:

obtaining, from an imaging device, one or more images of the test skin including the surgical staples;

applying an object detection model to the one or more images to infer respective locations of the surgical staples and infer respective classes of the surgical staples, wherein the object detection model is trained from a set of training images according to a first machine learning process;

mapping the respective locations to respective staple positions in an expected staple pattern and associating the respective classes with the respective locations to derive a staple map;

applying a keypoint detection model to the one or more images to infer locations of a set of keypoints of the surgical staples, wherein the keypoint detection model is trained from the set of training images according to a second machine learning process;

computing respective staple heights for each of the surgical staples based on the locations of the set of keypoints;

generating a digital inspection report based on inspection data including the staple map, the respective classes of the surgical staples, and the respective staple heights of the surgical staples; and outputting the digital inspection report to a user interface of a user device.

13. The non-transitory computer-readable storage medium of claim 12, wherein the respective classes of the surgical staples are selected from at least one class of defectively formed staples and at least one class of properly formed staples.

14. The non-transitory computer-readable storage medium of claim 13, wherein the at least one class of defectively formed staples included a first class associated with a defectively formed left staple leg, a second class associated with a defectively formed right staple leg, and a third class associated with a defectively formed right staple leg.

15. The non-transitory computer-readable storage medium of claim 12, wherein the set of keypoints includes a first peak of a first formed staple leg, a second peak of a second formed staple leg, a first crown point on a crown below the first peak, and a second crown point on the crown below the second peak.

16. The non-transitory computer-readable storage medium of claim 12, wherein the one or more images includes a left-side subset of images of the test skin captured from a left side perspective view and a right-side subset of images of the test skin captured from a right side perspective view.

17. The non-transitory computer-readable storage medium of claim 16, wherein deriving the staple map comprises:

generating a left staple map derived from the left-side subset of images;

generating a right staple map derived from the right-side subset of images; and merging the left staple map and the right staple map to resolve discrepancies according to a predefined set of merging rules.

18. The non-transitory computer-readable storage medium of claim 12, further comprising:

obtaining a defect classification model trained in a third machine learning process;

applying the defect classification model to at least a subset of the inspection data to infer one or more classes of defects in the surgical stapler or cartridge from which the surgical stapler fires the surgical staples; and wherein the digital inspection report further identifies the one or more classes of defects.

19. The non-transitory computer-readable storage medium of claim 12, further comprising:

obtaining a set of design parameters for the surgical stapler and a cartridge from which the surgical stapler fires the surgical staples;

storing the inspection data in association with a set of design parameters relating to the surgical stapler in a device model training dataset for training a device model;

applying a machine learning process to train the device model based on the device model training set; and obtaining input design parameters for a modified surgical stapler; and applying the device model to the input design parameters to infer a set of inferred inspection data for the modified surgical stapler.

20. An automated inspection processing device comprising:

one or more processors; and a non-transitory computer-readable storage medium storing instructions for automatically inspecting surgical staples fired into a test skin by a surgical stapler, the instructions when executed causing the one or more processors to perform steps comprising:

obtaining, from an imaging device, one or more images of the test skin including the surgical staples;

applying an object detection model to the one or more images to infer respective locations of the surgical staples and infer respective classes of the surgical staples, wherein the object detection model is trained from a set of training images according to a first machine learning process;

mapping the respective locations to respective staple positions in an expected staple pattern and associating the respective classes with the respective locations to derive a staple map;

applying a keypoint detection model to the one or more images to infer locations of a set of keypoints of the surgical staples, wherein the keypoint detection model is trained from the set of training images according to a second machine learning process;

computing respective staple heights for each of the surgical staples based on the locations of the set of keypoints;

generating a digital inspection report based on inspection data including the staple map, the respective classes of the surgical staples, and the respective staple heights of the surgical staples; and outputting the digital inspection report to a user interface of a user device.

* * * * *